United States Patent
Seo

(10) Patent No.: US 12,227,760 B2
(45) Date of Patent: Feb. 18, 2025

(54) WET GRANULATED CELL CULTURE MEDIUM AND PREPARATION METHOD THEREFOR

(71) Applicant: AMBROTHIA, LLC, Daejeon (KR)

(72) Inventor: Hee Kyo Seo, Gumi-si (KR)

(73) Assignee: AMBROTHIA, LLC, Daejeon (KR)

( * ) Notice: Subject to any disclaimer, the term of this patent is extended or adjusted under 35 U.S.C. 154(b) by 763 days.

(21) Appl. No.: 17/521,401

(22) Filed: Nov. 8, 2021

(65) Prior Publication Data

US 2022/0056403 A1 Feb. 24, 2022

Related U.S. Application Data

(63) Continuation-in-part of application No. 15/320,895, filed as application No. PCT/KR2015/006344 on Jun. 23, 2015, now abandoned.

(30) Foreign Application Priority Data

Jul. 7, 2014 (KR) .................. 10-2014-0084634

(51) Int. Cl.
| | |
|---|---|
| B01J 2/16 | (2006.01) |
| B01J 2/04 | (2006.01) |
| C12N 1/20 | (2006.01) |
| C12N 5/00 | (2006.01) |
| C12N 5/07 | (2010.01) |
| C12N 5/071 | (2010.01) |

(52) U.S. Cl.
CPC .............. *C12N 5/0602* (2013.01); *B01J 2/04* (2013.01); *C12N 1/20* (2013.01); *C12N 5/0025* (2013.01); *C12N 5/0601* (2013.01)

(58) Field of Classification Search
CPC .......................................................... B01J 2/16
See application file for complete search history.

(56) References Cited

U.S. PATENT DOCUMENTS

| | | | |
|---|---|---|---|
| 6,383,810 B2 | 5/2002 | Fike et al. |
| 6,627,426 B2 | 9/2003 | Biddle et al. |
| 7,572,632 B2 | 8/2009 | Fike et al. |
| 2001/0049141 A1 | 12/2001 | Fike et al. |
| 2002/0015999 A1 | 2/2002 | Biddle et al. |
| 2003/0153079 A1 | 8/2003 | Fike et al. |
| 2004/0022666 A1 | 2/2004 | Biddle et al. |
| 2004/0087022 A1 | 5/2004 | Fike et al. |
| 2006/0003447 A1 | 1/2006 | Fike et al. |

(Continued)

FOREIGN PATENT DOCUMENTS

| | | |
|---|---|---|
| JP | 2014054267 A | 3/2014 |
| KR | 1020100012361 A | 2/2010 |

(Continued)

OTHER PUBLICATIONS

CHO CD EfficientFeedTM B AGTTM Nutrient Supplement, gibco by life technologies.
D. Jayme et al., "A Novel Application of Granulation Technology to Improve Physical Properties and Biological Performance of Powdered Serum-Free Culture Media", Basic & Applied Aspects, pp. 155-159, vol. 12.

(Continued)

*Primary Examiner* — Jeanette M Lieb
*Assistant Examiner* — Paul C Martin
(74) *Attorney, Agent, or Firm* — Rabin & Berdo, P.C.

(57) ABSTRACT

Disclosed is a wet granulated cell culture medium and a preparation method therefor and, more specifically, to a wet granulated cell culture medium which supports the growth of mammalian cells and/or insect cells and/or plant cells and bacteria, and a preparation method therefor.

1 Claim, 9 Drawing Sheets

(56) References Cited

U.S. PATENT DOCUMENTS

| | | |
|---|---|---|
| 2006/0003448 A1 | 1/2006 | Fike et al. |
| 2006/0210640 A1 | 9/2006 | Kerkhof |
| 2006/0270038 A1 | 11/2006 | Fike et al. |
| 2006/0275886 A1 | 12/2006 | Fike et al. |
| 2008/0019883 A1 | 1/2008 | Fike et al. |
| 2008/0261308 A1 | 10/2008 | Fike et al. |
| 2011/0129926 A1 | 6/2011 | Fike et al. |
| 2011/0189344 A1 | 8/2011 | Bodo et al. |
| 2012/0276630 A1 | 11/2012 | Fike et al. |
| 2013/0065300 A1 | 3/2013 | Fike et al. |

FOREIGN PATENT DOCUMENTS

| | | |
|---|---|---|
| KR | 1020110028272 A | 3/2011 |
| KR | 1020140032370 A | 3/2014 |
| WO | 0236735 A2 | 5/2002 |
| WO | 2009152176 A2 | 12/2009 |

OTHER PUBLICATIONS

Innovative Technology for Granules and Pellets—Glatt.

JC Lupis, "Advanced Granulation Technology TM (AGT TM dry media format) Culture Media: Benefits and Case Studies", Deets Beat, Inc. White Paper, May 2014.

Nikowitz et al. (Powder Technology, vol. 205, pp. 155-159; 2010).

Orapin P. Rubino "Fluid-Bed Technology", Pharmaceutical Technology, Jun. 1999, pp. 104-113, vol. 6, No. 23.

Richard Fike et al., "Advance Granulation Technology", Cytotechnology, 2001, pp. 33-39, vol. 36.

Saurabh Srivastava et al., "Fluid Bed Technology: Overview and Parameters for Process Selection", International Journal of Pharmaceutical Sciences and Drug Research, 2010, pp. 236-246, vol. 2, No. 4.

Wong, PM et al., "Investigation on Side-Spray Fluidized Bed Granulation with Swirling Airflow", AAPS PharmSciTech, Mar. 2013, pp. 211-221, vol. 14, No. 1.

"Prior Art"

WET GRANULATED CELL CULTURE MEDIUM AND PREPARATION METHOD THEREFOR

CROSS REFERENCE TO PRIOR APPLICATIONS

This application is a continuation-in-part of U.S. patent application Ser. No. 15/320,895 filed Dec. 21, 2016, now abandoned, which is the National Stage Application of PCT International Patent Application No. PCT/KR2015/006344 filed on Jun. 23, 2015, under 35 U.S.C. § 371, which claims priority to Korean Patent Application No. 10-2014-00846364 filed on Jul. 7, 2014, which are all hereby incorporated by reference in their entirety.

TECHNICAL FIELD

The present invention relates to a wet granulated cell culture medium and a preparation method therefor and, more specifically, to a wet granulated cell culture medium which supports the growth of mammalian cells and/or insect cells and/or plant cells and bacteria, and a preparation method therefor.

BACKGROUND ART

A cell culture medium supports and maintain the growth of cells in artificial environments.

According to the types of the organisms in that the growth thereof is supported, the cell culture medium may include different components of over 10 or sometimes 100.

Typically, the culture medium required for the growth of mammalian cells, insect cells, or plant cells may be more complicated in comparison with a minimal medium sufficient to support the growth of bacteria and yeast.

In the initial studies of the cell culture, it utilizes the culture medium including undefined components for example, plasma, serum, embryonic extracts, other non-restrictively biological extracts or peptone. Therefore, it has developed with the development of a chemically defined culture medium. Usually, the chemically defined culture medium is not limited exclusively thereto, but it includes amino acids, vitamins, metal ions, an antioxidant, a chelator, growth factors, buffers, hormones, chlorides, and other materials publicly known to persons skilled in the art.

Some cell culture mediums are provided as a sterile and aqueous liquid. The disadvantage of a liquid cell culture medium is a reduced shelf-life and difficulties of handling and storage. As a result, many cell culture mediums are provided as a dry powder mixture, which is finely milled. It is dissolved in water and/or aqueous solution to be prepared. Also it is proposed in a state of being dissolved together with the other supplements for the growth of biological cells so as to prepare biological drugs from substantial nutritional base and/or part of the cells.

The handling of finely pulverized powder has a significant disadvantage. For example, it is very difficult to handle in bulk. Especially, where a part of each raw material is bad for the health, it may cause health problems for worker of handling the materials. Also, although each component is not toxic, there are health problems to the works owing to the high level dust itself in the respirable air and the amount of the dust in the air strictly controlled in many countries. Moreover, when the amount of dust is excessive or the warning measured is insufficient to prevent the ignition by a spark, it can cause a dust explosion.

Additionally, adverse carrying conditions can be occurred in long-term carrying conditions in that at least one lighter component among dry powder mediums is moved to the surface thereof or at least one heavier component is moved to the bottom of the primary packing. The localized high concentrations and the deficiency of each component in the physical center of the mass material may be negative in many ways in terms of the production quality of the medium. In addition, a de-mixing can have more influence on the patterning of oligosaccharide vital absolutely to a biopharmaceutical quality of directly delivering the medium quality to patients, rather than the physical deficiency and the concentration of each component, for example, the production of target pharmaceutical molecules per the medium.

In another aspect using the dry powder medium finely milled, there is a difficulty of the dissolution of the fine powder in the aqueous solution for preparing a final aqueous cell culture medium. Also, it is very difficult to wet the fine-milled powder and dissolve it in the aqueous solution. Therefore, the handling of the powder medium and the use thereof are very complicated.

On account of a limitation of the dry powder medium on a stability, a mixing and a dissolution thereof, the medium of the dry form can be manufactured without important supplements for example, carbonates, hydrolysates, growth factors, and other microelements (the final user will replenish them when the liquid is prepared from the dry powder medium). Additional treats and supplements thereof will increase the potential on very minor errors and labors.

Powdered bacterial cell culture media may be produced by molding the granulated powder into small granules. The result is small and uniform particles having the benefit of the stability, the handling, and the performance.

U.S. Pat. No. 6,383,810 B2 of Invitrogen corporation discloses a method for preparing a concentrated culture medium powder of eukaryotic cells. In the method thereof, it wets the dry powder cell culture medium by using a solvent and dries the wetted culture medium to obtain the dried and condensed cell culture medium.

This process has a big defect in that the entire medium components should be contacted with the water and the heating is required to remove the water. Thus, it can cause a significant side reaction of the medium components and a destruction or a deformation of the sensitive components with an unexpected result on the quality of the medium.

As a result, it is clearly necessary to discover a new form of the culture medium of mammalian cells and/or insect cells and/or plant cells and bacteria without causing the destruction and/or the side reaction of the medium components while being easily treating it.

In addition, in order to supplement the clear disadvantage of the conventional powder type medium or dry granular type medium, attempts in the method capable of deriving the performance of the maximum circular medium through a minimal heat and a containing of additives have been required.

FIG. 1 is a perspective view illustrating a drying and pressing equipment in accordance with the prior art.

Referring to FIG. 1, a roll press is shown as rolls (R1) and (R2) and a powder mixture (P1) is supplied to the roll press from the reservoir.

The compressed mixture come out from the roll press is standardized by a sieve (S). Parts of the product are removed for additional processing and packaging and parts (P2) of the powder having a particle size of less than 0.2 mm is subsequently reintroduced into the feed of the roll press.

In the Patent Literature 1, it solves partly the problem in that the dry powder mixture is finely powdered. However, the resultant product of the Patent Literature 1 is not uniform in shape and has an angular form.

Accordingly, since it bumps against each other to be broken during carrying and handling thereof, the granular shape is not properly maintained and parts thereof are re-formed into a fine powder. In other words, it is necessary to more increase the strength of the granular shape or change them into a circular shape. In addition, since it has difficulty in quantification thereof owing to an uniform shape of the particles, it is difficult to achieve an appropriate concentration of the medium.

PATENT LITERATURE

Patent Literature 1: Korean Patent Laying-open Gazette No. 10-2014-0032370 (Mar. 14, 2014)

DISCLOSURE

Technical Problem

The present invention has been made in an effort to solve the problems of the conceptual description of the conventional art as described above, and the objective of the present invention is to provide a medium with granules of which has a high strength and a uniform shape and size.

Also, the present invention is to greatly improve productivity by not using additional processes involving a spray drier, mixing, pulverization, etc., allowing making granules with a single process, the number of which is relatively less than that of conventional methods, and granulizing 100% of the prepared powders.

Technical Solution

It has been found that peptone containing/free or chemically defined mammalian, insect, plant and bacteria cell culture media can be produced in a wet granulated form by dissolving the mixed, finely milled powders of the dry medium components in purified water at a certain ratio and then spraying them in a fluid bed dryer.

No additives or coagulants are needed to aid the process.

The wet granulated cell culture media according to the present invention have a shape and strength superior to those of conventional granulated products, are excellent in appearance, are resistant to moisture and thus have a long shelf life, are easy to handle and pack, and can be produced under mild conditions so that no side reactions occur resulting from heating the medium components during the process of production.

Thus, the present invention relates to a wet granulated cell culture medium and preparation method therefor which include the following:
  (a) the step of providing a cell culture medium, in which the powders of the medium components are mixed or separate,
  (b) the step of dissolving the powders of the medium components, as a mixture or individually, in purified water at a certain ratio, and
  (c) spraying and granulating the dissolved cell culture medium with the bottom spray of a fluid bed.

In a preferred embodiment, the cell culture medium that is provided in step (a) is a bacteria cell culture medium.

In a preferred embodiment, the cell culture medium that is provided in step (a) may comprise one or more saccharide components, one or more amino acids, one or more vitamins, one or more salts, one or more buffer components, one or more co-factors, one or more nucleic acids, tryptones or peptones.

In a preferred embodiment, the equivalent ratio of purified water to cell culture medium in the cell culture medium that is provided in step (b) may be 0.5-3.

In a preferred embodiment, step (c) is performed by the following steps:
  (c1) feeding a cell culture medium solution to the bottom spray with a pump,
  (c2) forming the cell culture medium sprayed by the bottom spray into fine particles by the high-pressure hot air blown from the bottom, and
  (c3) forming the cell culture medium particles sprayed by the bottom spray into spherical granules due to the surface tension generated by the bottom spray of performing continuous spraying.

In a preferred embodiment, the pump of (c1) feeds the dissolved cell culture medium into the bottom spray at a speed between 180 ml/min and 500 ml/min.

In a preferred embodiment, the temperature of the hot air of (c2) ranges from 60° C. to 110° C.

In a preferred embodiment, the volume of the hot air of (c2) ranges from 500 $m^3$/hour to 6,000 $m^3$/hour.

Advantageous Effects

According to the wet granulated cell culture medium and the preparation method thereof of the present invention having the above constructions and actions, it relates to the wet granulated cell culture medium, especially, to the wet granulated cell culture medium which supports the growth of mammalian cells and/or insect cells and/or plant cells and bacteria and is to provide the medium with granules of which has a high strength and a uniform shape and size. The wet granulated cell culture media according to the present invention have a shape and strength superior to those of conventional granulated products, are excellent in appearance, are resistant to moisture and thus have a long shelf life, are easy to handle and pack.

According to the appliance of the present invention, the granules are prepared by spraying an aqueous cell culture medium solution which uses only clean purified water as the solvent, without adding an additional enhancer, adhesive, binder, coating material, co-solvent, etc. to a cell culture medium fed into a fluid bed processing system. Thus, the granules of the present invention are highly soluble when dissolved for use and excellent in flowability and thus have a greatly improved usability.

There is another effect capable of greatly improving productivity by not using additional processes involving a spray drier, mixing, pulverization, etc., allowing making granules with a single process, the number of which is relatively less than that of conventional methods, and granulizing 100% of the prepared powders.

BRIEF DESCRIPTION OF DRAWINGS

The above and other objects, features and advantages of the present invention will be more apparent from the following detailed description taken in conjunction with the accompanying drawings, in which:

FIG. 10A shows the cell culture medium granules (irregular and smaller shapes) made by a fluid bed with the cylindrical partition surrounding the bottom spray, and FIG. 10B shows the spherical cell culture medium granules (homogeneous, larger spherical granules) made by a fluid bed without a cylindrical partition according to the present invention;

REFERENCE SIGNS LIST

Figure 1:
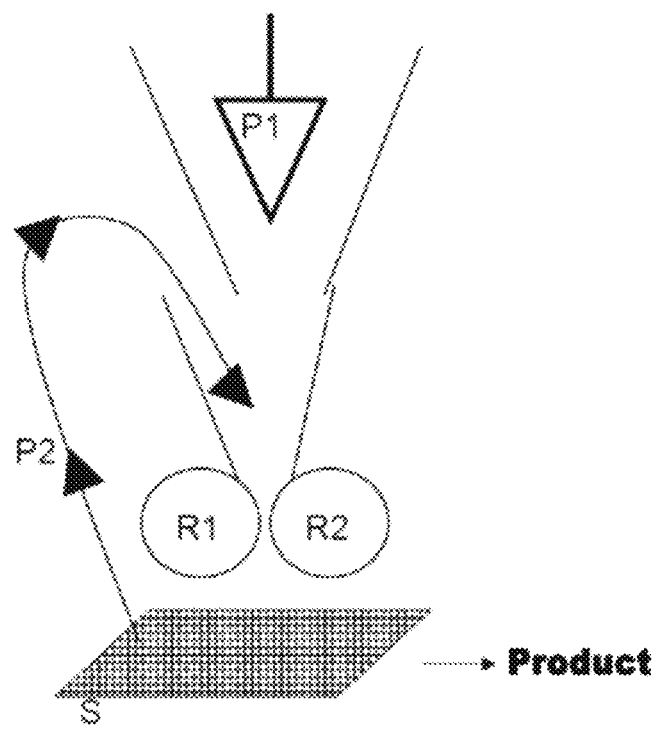
FIG. 1 is a perspective view illustrating a drying and pressing equipment in accordance with the prior art.

210: Step of preparation of aqueous cell culture medium solution
2203: Step of forming the droplets of the aqueous cell culture medium solution sprayed by the bottom spray into spherical granules due to the surface tension generated by the bottom spray of performing continuous spraying
2204: Step of drying spherical granules
300: Fluid bed processing system
310: Arrow at the bottom
330: Form fluidized by hot air
400: Fluid bed processing system
420: Blower
430: Aqueous solution storage
450: Bottom spray nozzle

BEST MODE

Mode for Invention

Hereinafter, the wet granulated cell culture medium according to the present invention and the preparation method therefor will be described more fully with reference to the accompanying drawings.

Figure 2:
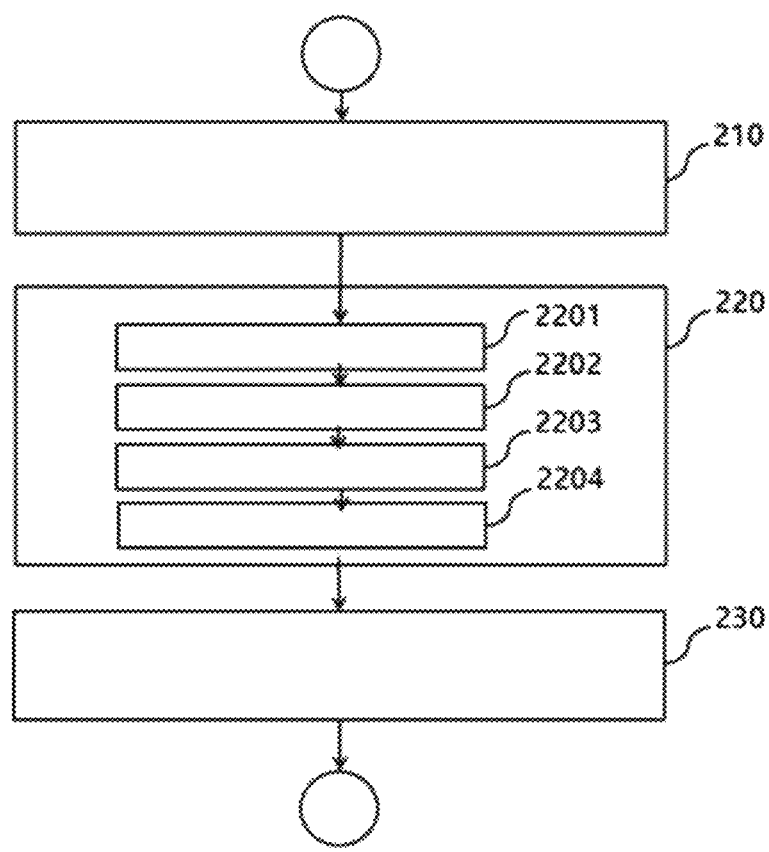
FIG. 2 is a block diagram of the preparation process of the wet granulated cell culture medium according to the present invention.

FIG. 2 is a block diagram of the preparation process of the wet granulated cell culture medium according to the present invention.

Referring to FIG. 2, the step of preparation of an aqueous cell culture medium solution (210) is illustrates.

The types of the cell culture media include mammalian, and/or insect and/or plant cell and bacteria culture media.

Examples of the animal cell culture media include DMEM, RPMI-1640, MCDB 131, MCDB 153, MDEM, IDEM, MEM, M199, McCoy s 5A, William's medium E, Leibovitz's L-15 medium, Grace's insect cell medium, IPL-41 insect cell medium, cell specific serum-free medium, etc., which are used for culturing keratin cells, epithelial cells, melanin cells, insect cells, etc.

Examples of the bacteria cell culture media include trypsin treated soy protein medium, ground brain-heart media, yeast extract media, peptone-yeast extract media, ground beef media, indole-nitrate media, LB media, YT media, SB media, SOB media, M9 minimal media, M63 minimal media, etc.

In a preferred embodiment of the cell culture medium, LB medium consists of tryptone, yeast extract and salt at the ratio of 2:1:2 as it is known.

In a preferred embodiment of the aqueous cell culture medium solution, the aqueous cell culture medium solution of LB medium is obtained by dissolving tryptone in water and dissolving yeast extract and salt in the same solution so that the equivalent ratio of tryptone, yeast extract and salt is 2:1:2.

The water is a solvent. Preferably, the water is distilled and/or deionized water, purified water or water for injection.

FIG. 2 illustrates the step of bottom spray granulation (220).

It is preferred that the size of granules ranges from 0.5 mm to 3.0 mm. If the size thereof is larger than those, the granules do not easily dissolve in water, and if the size thereof is smaller than those, the granules still have the problems of the conventional technology.

The aqueous cell culture medium solution should be ready to be fed to a fluid bed processing system through a pump and sprayed.

The step of bottom spray granulation (220) can be subdivided into the following steps, which are described in more detail below.

The step of feeding the aqueous cell culture medium solution to a bottom spray with a pump (2201) means feeding the aqueous medium solution prepared at the step of preparation of an aqueous medium solution (210) to a fluid bed processing system.

In the step where the droplets of the aqueous cell culture medium solution sprayed by the bottom spray are formed into fine particles by the hot air blown from the bottom (2202), preferably, the temperature of the hot air ranges from 60° C. to 110° C. and the volume of the hot air ranges from 500 m³/hour to 6,000 m³/hour. Also, it is preferred that the feeding speed of the aqueous cell culture medium solution sprayed by the bottom spray range from 180 ml/min to 500 ml/min.

In the step where the droplets of the aqueous cell culture medium solution sprayed by the bottom spray are formed into spherical granules due to the surface tension generated by the bottom spray of performing continuous spraying (2203), further layers are formed onto the surface of the fine particles generated at the step where the droplets of the aqueous cell culture medium solution sprayed by the bottom spray are formed into fine particles by the hot air blown from the bottom (2202), due to the droplets of aqueous cell culture medium solution continuously sprayed, so that the particles become spherical.

Preferably, in the step of feeding the aqueous cell culture medium solution to a bottom spray with a pump (2201), the step where the droplets of the aqueous cell culture medium solution sprayed by the bottom spray are formed into fine particles by the hot air blown from the bottom (2202), and the step where the droplets of the aqueous cell culture medium solution sprayed by the bottom spray are formed into spherical granules due to the surface tension generated by the bottom spray of performing continuous spraying (2203), the aqueous cell culture medium solution consists of 0.5 to 3 parts by weight of purified water with respect to 1 part by weight of cell culture medium.

The medium prepared according to the present invention is prepared as a high concentration solution because a seed, coagulant, enhancer, adhesive, binder, coating material, etc. other than the components of the aqueous cell culture medium solution cannot be additionally added.

In other words, the high concentration is to allow the droplets of aqueous solution sprayed and dispersed to be dried by hot air and the resultant fine particles in the form of powder to act as a seed, so that seeds are formed autonomously without provision of a separate seed.

In addition, the droplets of aqueous solution continuously sprayed adhere to the fine particles formed above and coat the surface thereof so that the fine particles are formed into granulated particles.

The step of drying spherical granules (2204) which are the resultant product of the step where the droplets of the aqueous cell culture medium solution sprayed by the bottom spray are formed into spherical granules due to the surface tension generated by the bottom spray of performing continuous spraying (2203), is performed in the same chamber.

In the step of drying spherical granules (2204), the pump for feeding the aqueous cell culture medium solution and the bottom spray for spraying the fed aqueous cell culture medium solution do not operate any more, and hot air generated by a heater is drawn out by a blower to fluidize the granules while adjusting the moisture content. Preferably, the moisture content of the spherical granules is 1 to 2%.

Theoretically, when using a fluid bed processing system, the moisture of liquid droplets of the aqueous cell culture medium solution sprayed into the fluid bed flow like a mist immediately evaporates to form fine powders, which act as seeds, even without seeds initially introduced into the product container, and abrasion between powders in the fluid bed flow leads to formation of cell culture medium granules.

However, it is difficult to control the conditions of initial fluidization and powder formation, and the initial phase takes a lot of time with a fluid bed with a cylindrical partition (480, shown with broken lines) surrounding the bottom spray, which suppresses spray drying and powder formation for coating process. For this reason, in the present invention, a fluid bed without a cylindrical partition (480, shown with broken lines) is needed to increase powder formation to act as a seed. It takes about 5 hours without a cylindrical partition to prepare granules of a desired shape and size, while it takes 10 hours with a cylindrical partition to prepare granules of a desired shape and size.

However, each of the steps above are performed in one apparatus as a single continuous process until the final products are obtained. This advantage allows convenience in operation, production efficiency and labor saving.

After all the steps above are completed, spherical granules are collected from the chamber and then filtered with a sieve to homogenize the size thereof. Granules of preferably 50 mesh or below may be introduced again into the aqueous solution prepared at the step of preparation of an aqueous cell culture medium solution (210) and used again at the step of bottom spray granulation (220) (the step of collecting spherical granules from the chamber and homogenizing the size of the granules (230)).

Figure 3:
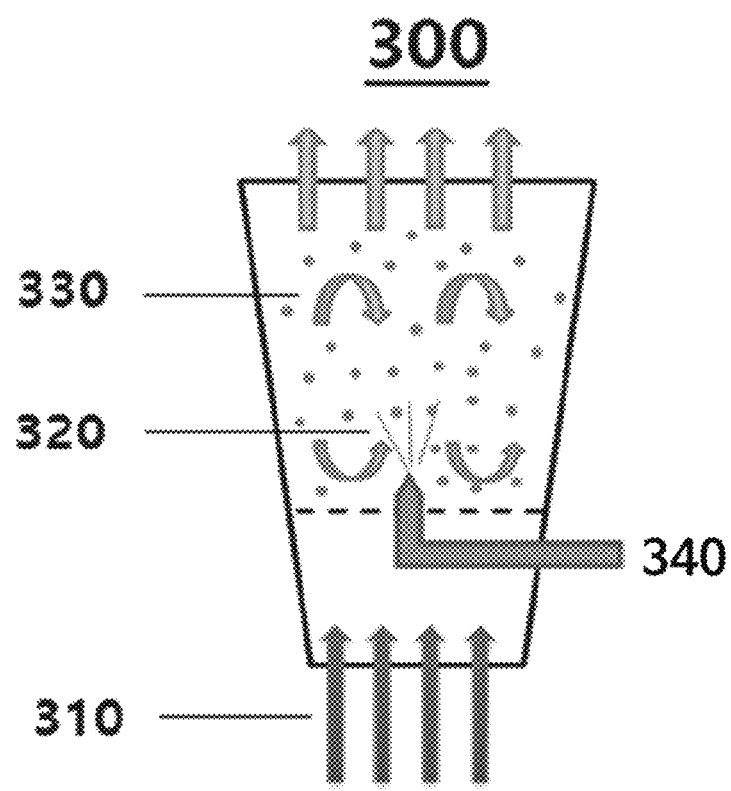
FIG. 3 shows an example of the fluid bed processing system.

FIG. 3 shows an example of the fluid bed processing system.

In FIG. 3, the arrow at the bottom (310) in the fluid bed processing system (300) indicates the direction toward which the hot air blows. The aqueous medium solution (320) is sprayed by a bottom spray nozzle (340) at the center of the fluid bed processing system (300) and fluidized by hot air (330). There is no cylindrical partition surrounding the bottom spray nozzle.

During this process, the aqueous medium solution is dried by hot air and during the drying process, the granules are homogenized into spherical ones due to surface tension. The dried media in the form of granules have a higher strength than the granules according to conventional technology and thus resolves the problems of thereof.

Figure 4:
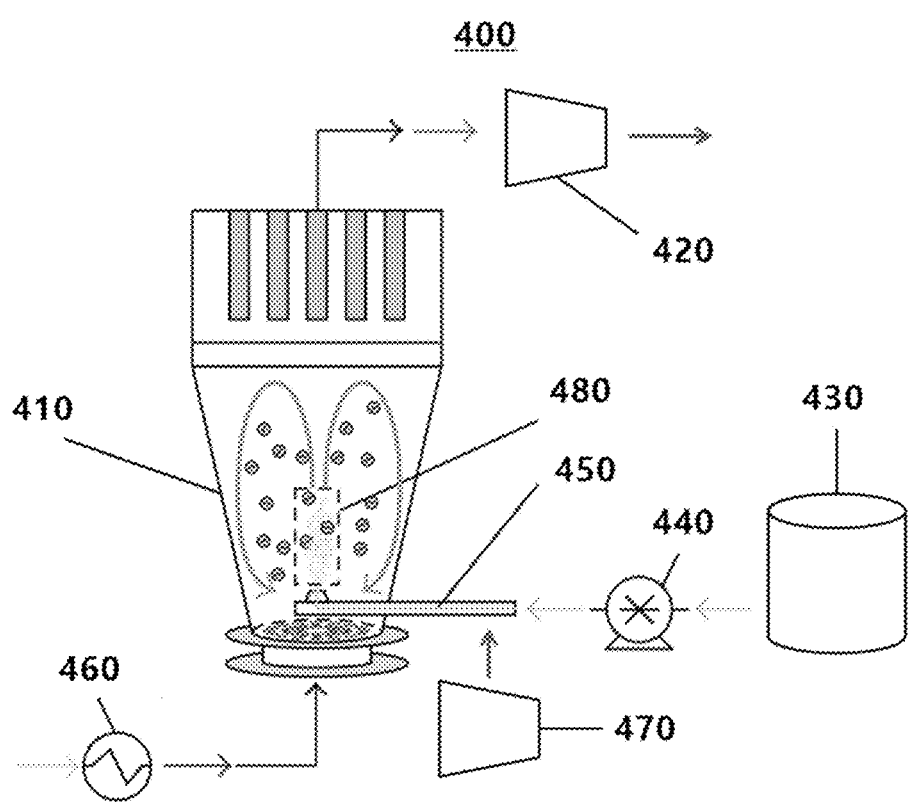
FIG. 4 shows a schematic diagram of a fluid bed processing system (400)

FIG. 4 shows a schematic diagram of a fluid bed processing system (400).

FIG. 4 illustrates a chamber (410), which is a room in which an aqueous cell culture medium solution is sprayed and is a fluidization region in which the droplets of an aqueous cell culture medium solution continuously sprayed flow.

In FIG. 4, a blower (420) located at the upper part of the chamber draws out hot air generate by a heater (460) to the outside to pass through the chamber.

An aqueous solution storage (430) stores the aqueous cell culture medium solution prepared at the step of preparation of aqueous medium solution (210). In order to suppress proliferation of microorganisms, it is preferred that the temperature of the aqueous solution storage (430) be 4° C. or less.

A pump (440) pulls out the aqueous solution in the aqueous solution storage (430) by applying a certain pressure in order to spray the solution into the chamber with an air compressor (470).

A bottom spray nozzle (450) is located at the lower part of the chamber and this consists of nozzles formed so as to allow the aqueous solution sprayed by the pump (440) with the air compressor (470) to form droplets. In the present invention, there is no cylindrical partition surrounding the bottom spray nozzle.

Figure 5:
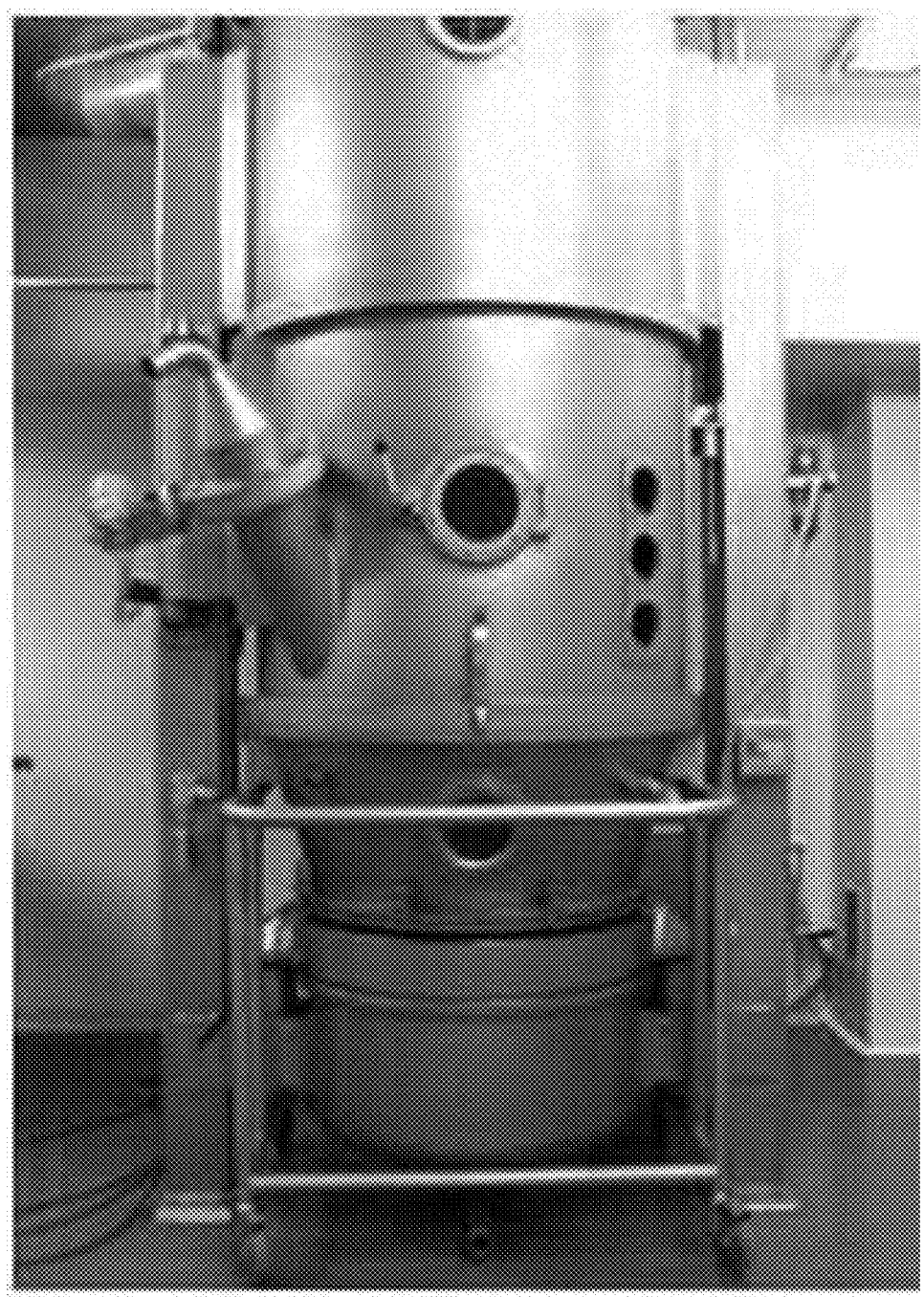
FIG. 5 shows an example of the apparatus for preparation of the wet granulated cell culture medium according to the present invention.

FIG. 5 shows an example of the apparatus for preparation of the wet granulated cell culture medium according to the present invention.

Figure 6:
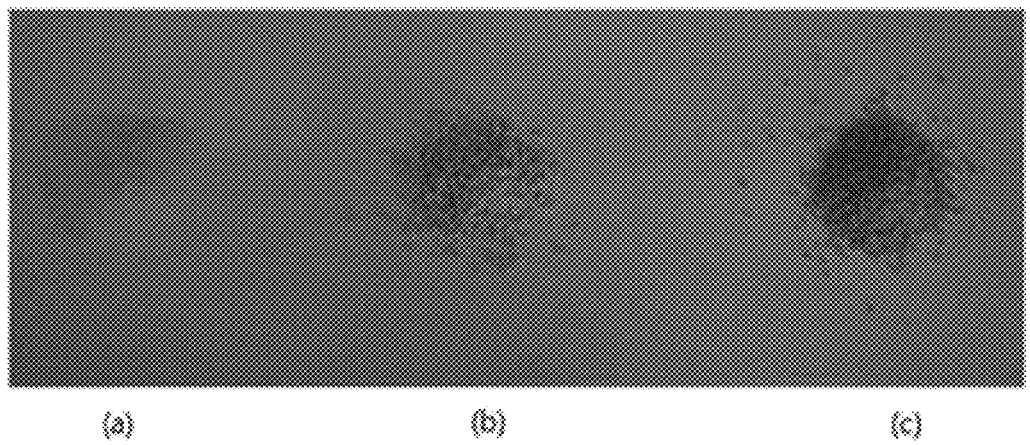
FIG. 6 shows the photographs of actual cell culture medium granules.

FIG. 6 shows the photographs of actual cell culture medium granules.

FIG. 6(a) shows conventional cell culture medium granules, FIG. 6(b) shows cell culture medium granules prepared by the improved method according to Patent Document 1, and FIG. 6(c) shows the spherical cell culture medium granules according to the present invention.

FIG. 6(a) shows finely milled powders, FIG. 6(b) shows irregular and angular shapes, and FIG. 6(c) shows the homogeneous spherical granules according to the present invention.

Figure 7:
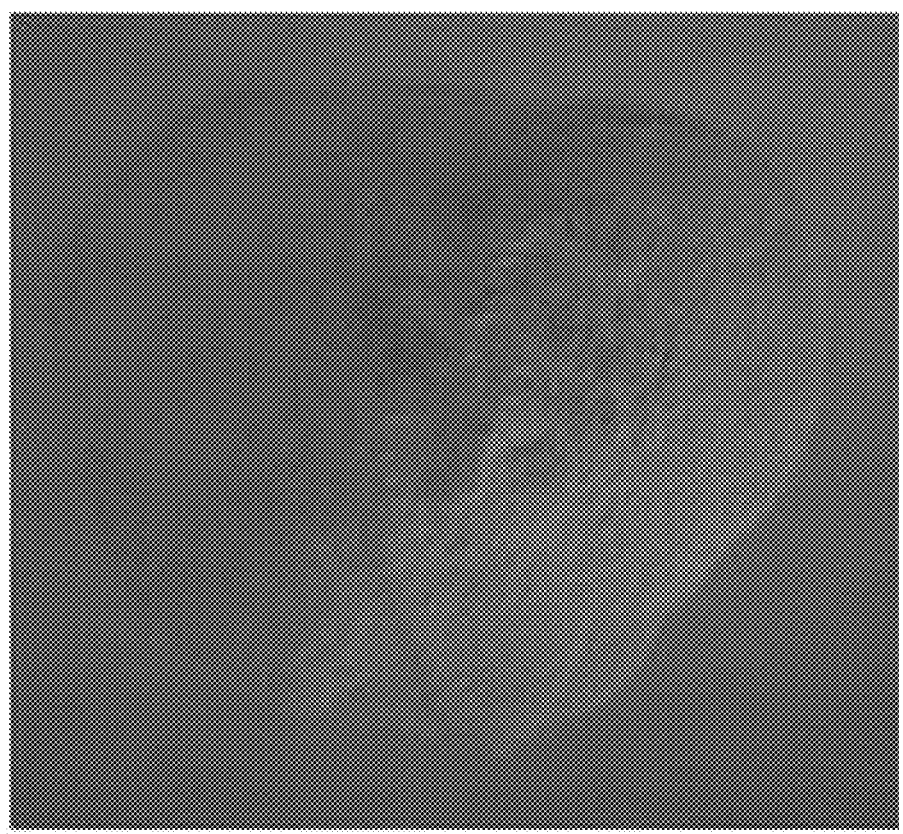
FIG. 7 shows an enlargement of the photograph of FIG. 6(*a*)

FIG. 7 shows an enlargement of the photograph of FIG. 6(a).

Figure 8:
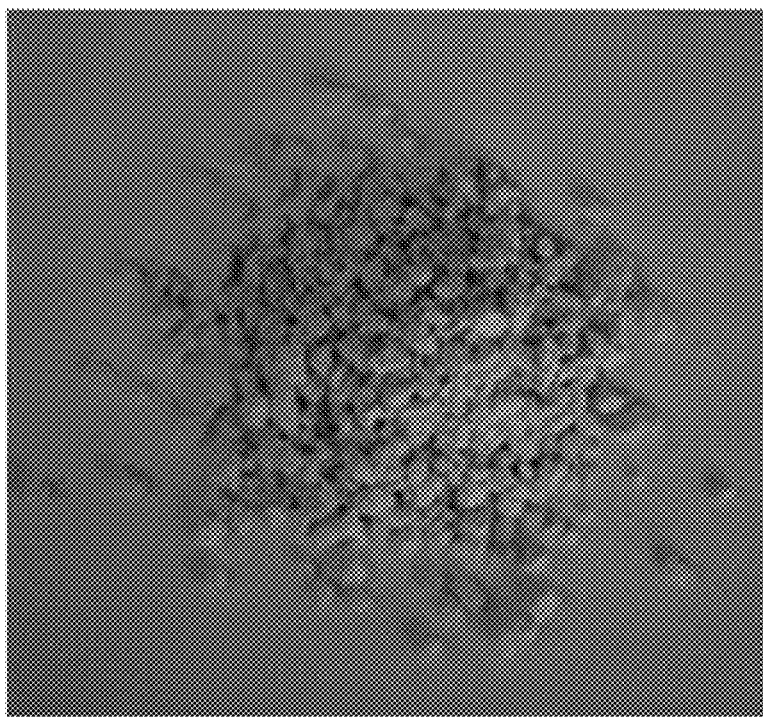
FIG. 8 shows an enlargement of the photograph of FIG. 6(*b*)

FIG. 8 shows an enlargement of the photograph of FIG. 6(b).

Figure 9:
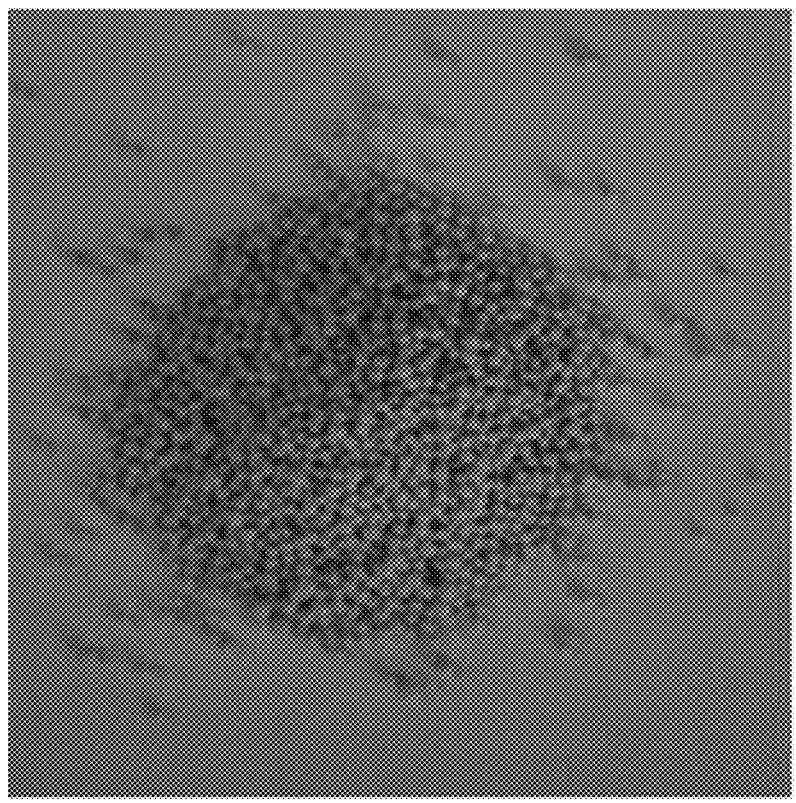
FIG. 9 shows an enlargement of the photograph of FIG. 6(*c*)

FIG. 9 shows an enlargement of the photograph of FIG. 6(c).

Figures 10A, 10B:
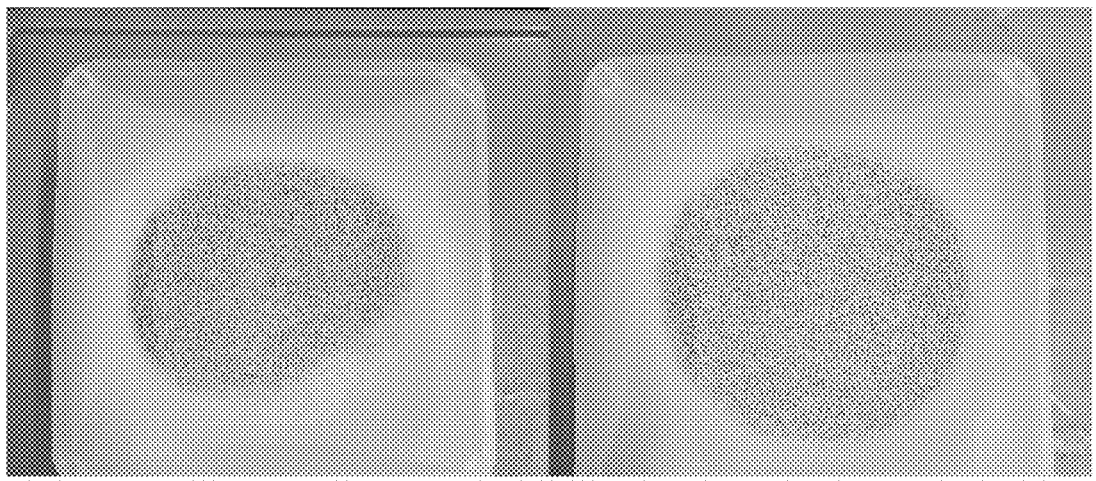
FIGS. 10A and 10B show the photographs of actual cell culture medium granules made by a bottom spray fluid bed with a cylindrical partition and without the cylindrical partition for 5 hours of process time.

FIGS. 10A and 10B show the photographs of actual cell culture medium granules made by a bottom spray fluid bed with a cylindrical partition and without the cylindrical partition for 5 hours of process time.

FIG. 10A shows the cell culture medium granules made by a fluid bed with a cylindrical partition surrounding the bottom spray for 5 hours of process time, and FIG. 10B shows the spherical cell culture medium granules made by a fluid bed without a cylindrical partition for 5 hours of process time according to the present invention.

FIG. 10A shows irregular and smaller shapes, and FIG. 10B shows the homogeneous, larger spherical granules according to the present invention.

Figure 11:
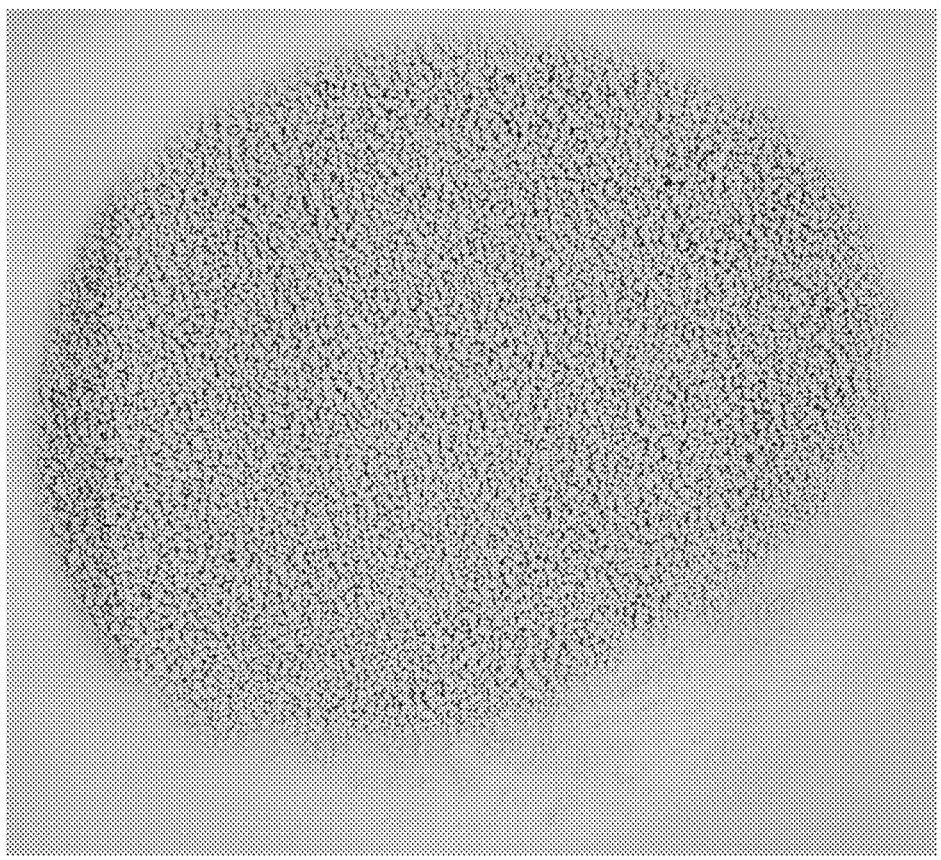
FIG. 11 shows an enlargement of the photograph of FIG. 10A.

FIG. 11 shows an enlargement of the photograph of FIG. 10A.

Figure 12:
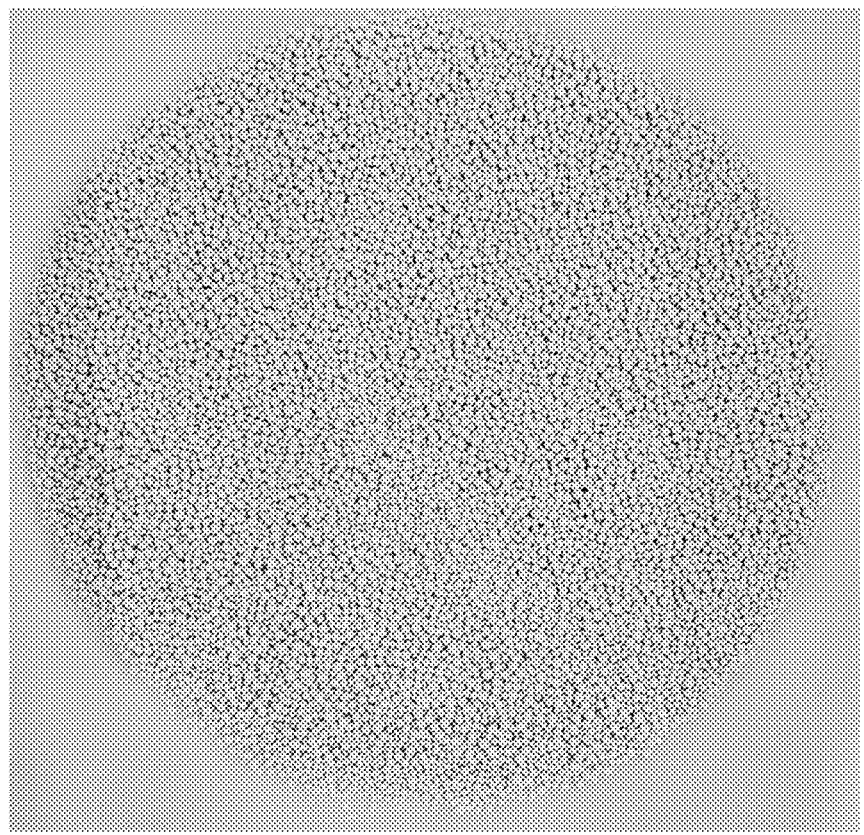
FIG. 12 shows an enlargement of the photograph of FIG. 10B.

FIG. 12 shows an enlargement of the photograph of FIG. 10B.

Figure 13:
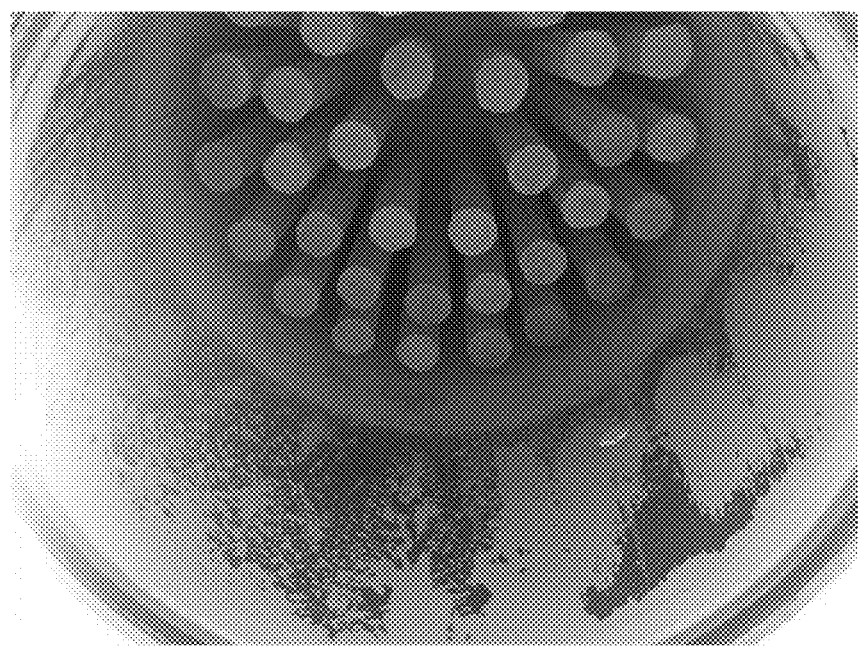
FIG. 13 shows the increment of fine powder formation act as a seed made by a fluid bed without a cylindrical partition surrounding the bottom spray.

FIG. 13 shows the increment of fine powder formation act as a seed made by a fluid bed without a cylindrical partition surrounding the bottom spray.

While the present invention has been described with respect to the specific embodiments, it will be apparent to those skilled in the art that various changes and modifications may be made without departing from the spirit and scope of the present invention as defined in the following claims.

INDUSTRIAL APPLICABILITY

According to the present invention, the granules are prepared by spraying an aqueous cell culture medium solution which uses only clean purified water as the solvent, without adding an additional enhancer, adhesive, binder, coating material, co-solvent, etc. to a cell culture medium fed into a fluid bed processing system. Thus, the granules of the present invention are highly soluble when dissolved for use and excellent in flowability and thus have a greatly improved usability. Therefore, the granules of the present invention are expected to be useful in the field of cell culture.

The invention claimed is:

1. A method for preparation of a cell culture medium, consisting of: providing a cell culture medium;
dissolving the cell culture medium in purified water to produce an aqueous cell culture medium solution, wherein the aqueous cell culture medium solution consists of 0.5 to 3 parts by weight of purified water with respect to 1 part by weight of cell culture medium;
feeding the aqueous cell culture medium solution to a bottom spray with a pump of a fluid bed, the fluid bed having a chamber in which the bottom spray is located at a bottom without a cylindrical partition surrounding the bottom spray, wherein the pump feeds the aqueous cell culture medium solution into the bottom spray at a speed between 180 ml/min and 500 ml/min;
spraying the aqueous cell culture medium solution into the chamber of the fluid bed via the bottom spray without adding separate seed or coagulant, wherein the aqueous cell culture medium solution sprayed via the bottom spray is formed into droplets;
drawing out hot air in the chamber via a blower of the fluid bed at a volume of 500 m$^3$/hour to 6,000 m$^3$/hour, a temperature of the hot air ranging 60° C. to 110° C., wherein the droplets of the aqueous cell culture medium are formed into fine particles due to absence of the cylindrical partition surrounding the bottom spray;
in the same chamber of the fluid bed, repeating the spraying step via the bottom spray to the fine particles to coat a surface thereof so that the fine particles are formed into spherical granules, wherein surface tension generated by repeating the spraying step forms the spherical granules;
drying the spherical granules by the hot air drawn out by the blower without the steps of feeding and spraying; and
collecting the spherical granules from the chamber of the fluid bed and homogenizing a size of the spherical granules, wherein a size of spherical granules ranges from 0.5 mm to 3.0 mm.

* * * * *